Oct. 10, 1939. P. ECKE Plant Pat. 343
POINSETTIA
Filed Oct. 26, 1938
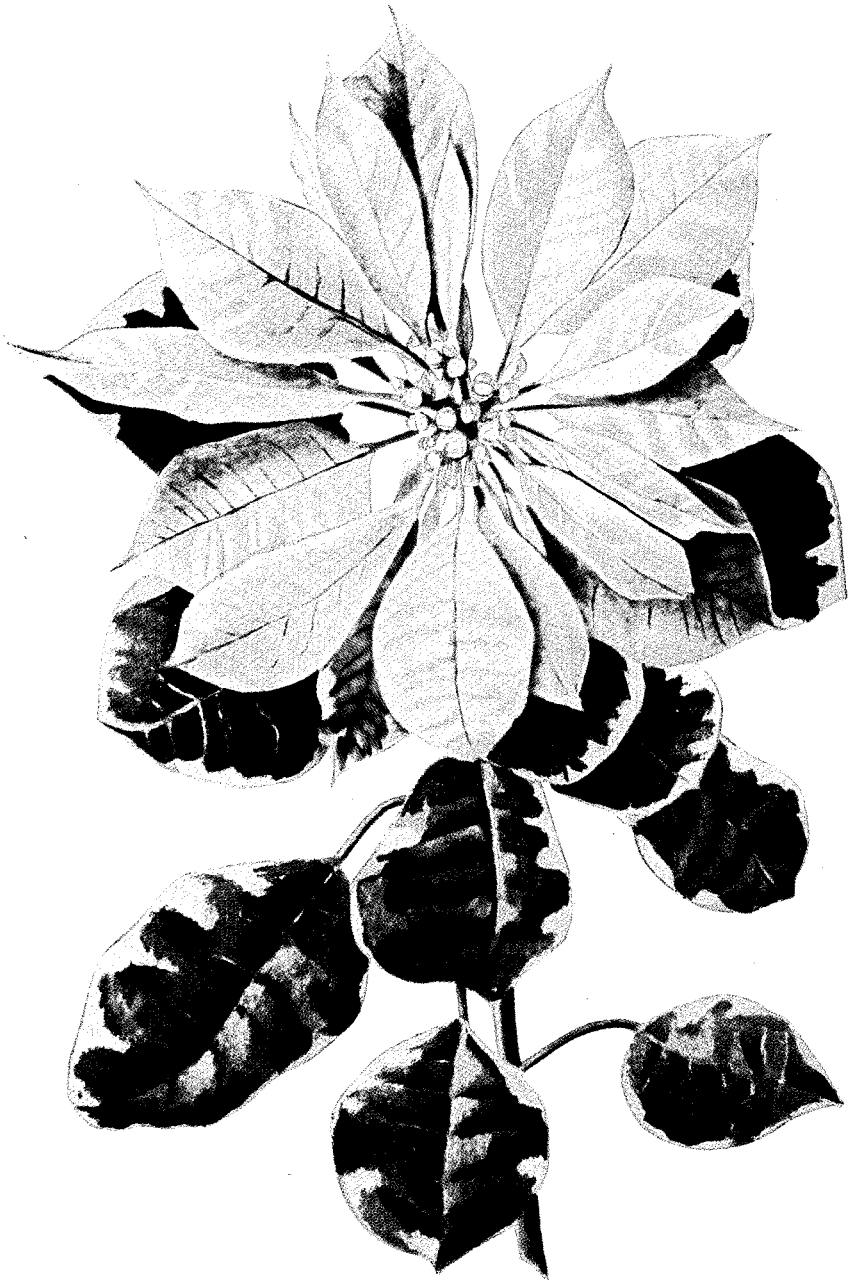
Inventor
Paul Ecke
By Robert Robb
Attorney Patented Oct. 10, 1939

Plant Pat. 343

UNITED STATES PATENT OFFICE

343

POINSETTIA

Paul Ecke, Encinitas, Calif.

Application October 26, 1938, Serial No. 237,160

1 Claim. (Cl. 47—60)

The present invention relates to a new and distinct variety of poinsettia, originating as a sport.

More specifically, in the spring of 1934 a sport of poinsettia (*Euphorbia pulcherrima*) was discovered on a poinsettia plant growing in the greenhouses of T. W. Reed, in Temple, Texas, and was taken to Encinitas, California, where it has been asexually propagated. It has remained true to type through the propagation of several thousand plants.

The colors herein mentioned correspond approximately with those shown and identified by the Robert Ridgway color standard and nomenclature, herein referred to by name and identified by the color name and plate of said color standard.

The accompanying painting, forming a part of this application, graphically shows the subject in its full maturity, which painting is a face view of the subject, showing it in its normal condition, with its grace and charm of appearance.

The following is a detailed description of the new variety:

*Structure*

The stems are long, stiff, and very strong, and are comparatively small in cross section. Their average length is four feet, with many small branches at the top, usually growing from three knob-like branches. Each branch bears several bracts and a few flowers.

*Petioles*

Extending outwardly from around each of the stems is a number of petioles, which are attached to and arranged spirally around their respective stems, with the inner or base portion spanning the interior of its respective stem; with their color similar to that of the stems, but more of a light "Terre Verte" color, shown on Plate XXXIII (BB–G, *i*).

*Leaves*

The shape of the leaves is ovate entire acuminate. They are not pinnatifid therefore being different in shape from the leaves on the Oak Leaf type poinsettias. Their color is variegated, having a mottled appearance on the upper side of the leaves, of dark, dull, yellow-green (Plate XXXII) marked at the edge with yellow, slightly deeper than Plate IV.

*Bracts*

The bracts are similar to the leaves, except that they are much smaller, are lanceolate in contour, do not protrude outwardly so far, and near their maturity they assume a color entirely different therefrom, which is that their upper or face sides are a "Jasper Red" as shown on Plate XIII and their under sides are a "Pale Salmon" color as shown on Plate XIV.

*Flowers*

A node is formed on the upper end of each peduncle, each of which usually presents three short and comparatively large heavy stem-like knobs, which protrude upward and expansively apart, each of which latter carries a flower of a "Pale Greenish Yellow" color, which is substantially as that shown on Plate V, which prior to maturity is almost white. Each of said flowers usually contains three ovules which, if properly impregnated, will germinate a new poinsettia. The nine to twelve flowers are very small and are surrounded by the bracts, which prior to maturity are almost white. Each flower usually develops three seeds and the seed pods are each about ¼-inch in diameter.

*Appearance*

When looking directly at the center of the bloom, that is, at the upper half of the painting, the leaves and bracts form the background of the flowers. Perhaps the most ornamental parts of this poinsettia are the colored bracts about a cluster of tiny flowers, which make an attractive combination.

*Thorns*

There is nothing of this nature in connection with this plant.

*Dimensions*

The total height of the plant at maturity is approximately eight feet, and the greatest lateral dimension is approximately five feet.

*Habits*

Vigorous, but slow in growth, easily cultivated, if properly handled, and persistent and perennial in growth.

*Immunity*

The entire plant seems to be immune from insects, disease, and all other obnoxious and detrimental interference.

*Aroma*

None apparent.

*Variations*

Each of the features mentioned regarding this plant is simply a replica of the same in all the others which I have produced; that is to say, there is very little, if any, difference in corresponding features. However, in comparison with the same grown in various localities, in different soil, and at various times of the year, in different temperature, or in different greenhouses, or in the open, and even by different persons, there may be some slight variations.

*Maintenance*

After being cut, the bloom and the foliage, with ample stem, and even without refrigeration, has the quality of keeping in excellent condition for a period of a week or ten days, depending upon the exterior conditions.

*Planting*

I have found by experience that if a cutting is taken and planted at any time from May until September, that the plant will mature in November, retaining its beauty for two months, after which it will remain dormant for about three months; however, the above estimate is subject to variations, depending on the climate and other conditions. It can be grown successfully anywhere in the United States and Canada in greenhouses kept at the proper temperature, but outdoors only in frost-free sections.

*Comparisons*

Compared with other species of poinsettias, the difference is principally that this new production presents foliage that is variegated and, therefore, more attractive than other species.

I claim:

A new and distinct variety of poinsettia substantially as shown and described, characterized especially by the variegated foliage which is ovate entire acuminate.

PAUL ECKE.